(12) United States Patent
Bottom

(10) Patent No.: US 10,610,659 B2
(45) Date of Patent: Apr. 7, 2020

(54) GAS MIXER INCORPORATING SENSORS FOR MEASURING FLOW AND CONCENTRATION

(71) Applicant: General Electric Company, Schenectady, NY (US)

(72) Inventor: Douglas Kirk Bottom, Watertown, WI (US)

(73) Assignee: GENERAL ELECTRIC COMPANY, Schenectady, NY (US)

( * ) Notice: Subject to any disclaimer, the term of this patent is extended or adjusted under 35 U.S.C. 154(b) by 226 days.

(21) Appl. No.: 15/467,462

(22) Filed: Mar. 23, 2017

(65) Prior Publication Data

US 2018/0272099 A1    Sep. 27, 2018

(51) Int. Cl.

| | |
|---|---|
| A61M 16/12 | (2006.01) |
| A61M 16/20 | (2006.01) |
| A61M 16/10 | (2006.01) |
| A61M 16/08 | (2006.01) |
| G01F 1/66 | (2006.01) |
| G01F 1/74 | (2006.01) |
| A61M 16/22 | (2006.01) |

(52) U.S. Cl.
CPC ........ *A61M 16/12* (2013.01); *A61M 16/0891* (2014.02); *A61M 16/104* (2013.01); *A61M 16/1005* (2014.02); *A61M 16/201* (2014.02); *A61M 16/22* (2013.01); *A61M 2016/102* (2013.01); *A61M 2202/0208* (2013.01); *A61M 2202/0275* (2013.01); *A61M 2205/3334* (2013.01); *A61M 2205/3368* (2013.01); *A61M 2205/3375* (2013.01); *G01F 1/667* (2013.01); *G01F 1/74* (2013.01); *Y10T 137/2509* (2015.04)

(58) Field of Classification Search
CPC .................... Y10T 137/2509; Y10T 137/2499
See application file for complete search history.

(56) References Cited

U.S. PATENT DOCUMENTS

| | | | |
|---|---|---|---|
| 4,425,805 A | 1/1984 | Ogura et al. | |
| 4,452,090 A | 6/1984 | Kou et al. | |
| 4,492,120 A | 1/1985 | Lewis et al. | |
| 4,581,942 A | 4/1986 | Ogura et al. | |

(Continued)

FOREIGN PATENT DOCUMENTS

| | | |
|---|---|---|
| EP | 0874238 | 10/1998 |
| EP | 0894506 | 2/1999 |

(Continued)

OTHER PUBLICATIONS

International Search Report and Written Opinion issued in connection with corresponding PCT Application No. PCT/US2018/023713 dated Jul. 11, 2018, 10 pages.

(Continued)

*Primary Examiner* — Robert K Arundale
(74) *Attorney, Agent, or Firm* — Fletcher Yoder, P.C.

(57) ABSTRACT

A medical gas mixer is provided. In one embodiment, dual-purpose sensors are employed, such as in a configuration in which one is positioned in the mixed gas flow channel and one is positioned in the main gas flow channel. The sensors provide measurements that may be used to determine both gas flow and gas concentration in the mixed and main gas channels, even when the identity and/or properties of the gas in the main gas channel are unknown.

17 Claims, 5 Drawing Sheets

(56) References Cited

U.S. PATENT DOCUMENTS

| | | |
|---|---|---|
| 4,611,590 A | 9/1986 | Ryschka et al. |
| 5,060,506 A | 10/1991 | Douglas |
| 5,060,514 A | 10/1991 | Aylsworth |
| 5,247,826 A | 9/1993 | Frola et al. |
| 5,369,979 A | 12/1994 | Aylsworth et al. |
| 5,470,511 A | 11/1995 | Laybourne et al. |
| 5,546,931 A | 8/1996 | Rusz |
| 5,581,014 A | 12/1996 | Douglas |
| 5,644,070 A | 7/1997 | Gibboney et al. |
| 5,645,071 A | 7/1997 | Harnoncourt et al. |
| 5,694,924 A | 12/1997 | Cewers |
| 5,957,129 A | 9/1999 | Tham et al. |
| 5,967,141 A | 10/1999 | Heinonen |
| 6,050,283 A * | 4/2000 | Hoffman .............. G05D 11/135 137/3 |
| 6,116,235 A | 9/2000 | Walters et al. |
| 6,131,571 A | 10/2000 | Lampotang et al. |
| 6,155,255 A | 12/2000 | Lambert |
| 6,275,650 B1 | 8/2001 | Lambert |
| 6,279,378 B1 | 8/2001 | Sheen et al. |
| 6,286,360 B1 | 9/2001 | Drezewiecki |
| 6,443,150 B1 | 9/2002 | Pessala et al. |
| 6,488,028 B1 | 12/2002 | Lambert |
| 6,506,608 B2 | 1/2003 | Mault |
| 6,634,239 B2 | 10/2003 | Gomm et al. |
| 6,745,771 B2 | 6/2004 | Castor et al. |
| 6,799,883 B1 * | 10/2004 | Urquhart .......... B01F 15/00227 137/3 |
| 7,063,668 B2 | 6/2006 | Cardelius et al. |
| 7,144,552 B1 * | 12/2006 | Fukuizumi .......... B01F 3/04248 422/62 |
| 7,434,580 B2 | 10/2008 | Downie et al. |
| 7,490,607 B2 | 2/2009 | Bottom et al. |
| 7,810,988 B2 * | 10/2010 | Kamimura .............. B01F 3/088 366/160.2 |
| 7,886,783 B2 | 2/2011 | Rindy et al. |
| 7,889,345 B2 | 2/2011 | Shang et al. |
| 8,336,544 B2 | 12/2012 | Downie |
| 8,361,231 B2 | 1/2013 | Kouketsu et al. |
| 8,365,724 B2 | 2/2013 | Bottom |
| 8,752,544 B2 | 6/2014 | Bottom |
| 8,752,548 B2 | 6/2014 | Larsson et al. |
| 8,794,237 B2 | 8/2014 | Wilkinson et al. |
| 9,289,569 B2 | 3/2016 | Cardelius et al. |
| 2003/0150456 A1 | 8/2003 | Wruck et al. |
| 2004/0093957 A1 | 5/2004 | Buess et al. |
| 2004/0149285 A1 | 8/2004 | Wallen |
| 2005/0288873 A1 | 12/2005 | Urdaneta et al. |
| 2006/0096760 A1 * | 5/2006 | Ohmer ................ E21B 43/01 166/304 |
| 2007/0107879 A1 | 5/2007 | Radomski et al. |
| 2009/0090472 A1 | 4/2009 | Radomski |
| 2010/0101571 A1 | 4/2010 | Messerges |
| 2010/0224264 A1 * | 9/2010 | Homan ................ B01F 3/028 137/93 |
| 2010/0269821 A1 | 10/2010 | Larsson et al. |
| 2011/0155131 A1 | 6/2011 | Bottom |
| 2012/0180724 A1 | 7/2012 | Kouketsu et al. |
| 2013/0239968 A1 | 9/2013 | Friberg et al. |
| 2014/0254305 A1 | 9/2014 | Caso et al. |
| 2017/0101715 A1 * | 4/2017 | Nishizato ............ C23C 16/4482 |
| 2018/0272098 A1 * | 9/2018 | Bottom ............. A61M 16/0891 |

FOREIGN PATENT DOCUMENTS

| | | |
|---|---|---|
| EP | 0965372 | 12/1999 |
| GB | 415048 | 8/1934 |
| GB | 2029572 | 3/1980 |
| GB | 2255912 | 11/1992 |
| WO | WO9820926 | 5/1998 |
| WO | WO2004087244 | 10/2004 |
| WO | WO2004091708 | 10/2004 |
| WO | WO2008145177 | 12/2008 |

OTHER PUBLICATIONS

Marioli. Daniele, et al.; "Digital Time-of-Flight Measurement for Ultrasonic Sensors", IEEE Transaction on Instrumentation and Measurement, vol. 41, No. 1, Feb. 1992, pp. 93-97.

* cited by examiner

GAS MIXER INCORPORATING SENSORS FOR MEASURING FLOW AND CONCENTRATION

BACKGROUND

The subject matter disclosed herein relates generally to the use of sensors capable of measuring both flow and concentration in a medical gas mixer, such as may be part of an anesthesia machine.

Conventional gas mixing devices, such as those used in the administration of anesthesia, typically blend together two or more known gases. Each gas is generally separately sourced and provided by a respective mixer input. After blending, the gases may be output as a mixed gas at a mixed gas channel output and may be administered to a patient.

In conventional mixer technology, prior information of each input gas identity and/or properties is needed for the gas mixing device to properly control flow and/or concentration of the mixed gas output. This requirement limits architectural flexibility with regards to what input gases may be sourced and dictates that they not be variable in composition. This requirement also tends to drive product cost higher (as the associated sensors must be calibrated for each specific possible input gas) and can result in reduced up-time, such as if an outside device is relied upon to supply the needed information about the input gas and communication with the outside device fails.

Conventional mixer technology also has other limitations. For example, in conventional architectures, additional sensors may be employed at the mixing device output so as to both provide control of flow and concentration at the device output and to provide an independent, redundant measurement of concentration for patient safety. In addition, providing accurate control of flow and/or concentration at the device output typically requires precise measurement of one or more local environmental conditions for the gas at both the input and output of the device. These additional requirements also act to increase system complexity and cost.

BRIEF DESCRIPTION

In one embodiment, a medical gas mixer is provided. In accordance with this embodiment, the medical gas mixer includes: a main gas channel comprising one or more main control valves that during operation control a first flow of a first gas through the main gas channel; a side gas channel, comprising one or more side channel control valves that during operation control a second flow of a second gas through the side gas channel; a mixed gas channel configured to receive the first flow of the first gas and the second flow of the second gas during operation and to output a mixed gas; a first dual-purpose sensor positioned in the main gas channel and configured to generate a first set of measurements during operation; a second dual-purpose sensor positioned in the mixed gas channel and configured to generate a second set of measurements during operation; and a gas mixer controller configured to receive the first set of measurements and the second set of measurements, to calculate, one or more of flow of the first gas, flow of one or more components of the first gas, or concentration of one or more components of the first gas, to calculate, one or more of flow of the mixed gas, flow of one or more components of the mixed gas, or concentration of one or more components of the mixed gas, and to control operation of one or more of the main channel control valves or one or more of the side channel control valves based upon one or more of the calculated flows or concentrations.

In a further embodiment, a method for regulating operation of a medical gas mixer is provided. In accordance with this embodiment, a first gas is flowed through a main gas channel. A second gas is flowed through a side gas channel. The first gas and the second gas are combined to form a mixed gas in a mixed gas channel. A first set of measurements is generated using a first dual-purpose sensor in the main gas channel and a second set of measurements is generated using a second dual-purpose sensor in the mixed gas channel. One or more of flow of the first gas, flow of one or more components of the first gas, or concentration of one or more components of the first gas is calculated using one or both of the first set of measurements or the second set of measurements. One or more of flow of the mixed gas, flow of one or more components of the mixed gas, or concentration of one or more of the components of the mixed gas is calculated using one or both of the first set of measurements or the second set of measurements. Operation of valves in one or more of the main gas channel or side gas channel is controlled based upon one or more of the calculated flows or concentrations.

In an additional embodiment, an ultrasonic sensor is provided. In accordance with this embodiment, the ultrasonic sensor comprises: a gas conduit having an inlet and an outlet; a first ultrasonic transducer positioned on the gas conduit; a second ultrasonic transducer positioned on the gas conduit downstream from the first ultrasonic transducer; and control circuitry configured to operate the first ultrasonic transducer and the second ultrasonic transducer, and to process signals received from the first ultrasonic transducer and the second ultrasonic transducer to generate a measurement set comprising an upstream time-of-flight and a downstream time-of-flight.

BRIEF DESCRIPTION OF THE DRAWINGS

These and other features, aspects, and advantages of the present invention will become better understood when the following detailed description is read with reference to the accompanying drawings in which like characters represent like parts throughout the drawings, wherein.

DETAILED DESCRIPTION

One or more specific embodiments will be described below. In an effort to provide a concise description of these embodiments, all features of an actual implementation may not be described in the specification. It should be appreciated that in the development of any such actual implementation, as in any engineering or design project, numerous implementation-specific decisions must be made to achieve the developers' specific goals, such as compliance with system-related and business-related constraints, which may vary from one implementation to another. Moreover, it should be appreciated that such a development effort might be complex and time consuming, but would nevertheless be a routine undertaking of design, fabrication, and manufacture for those of ordinary skill having the benefit of this disclosure.

When introducing elements of various embodiments of the present disclosure, the articles "a," "an," "the," and "said" are intended to mean that there are one or more of the elements. The terms "comprising," "including," and "having" are intended to be inclusive and mean that there may be additional elements other than the listed elements. Furthermore, any numerical examples in the following discussion are intended to be non-limiting, and thus additional numerical values, ranges, and percentages are within the scope of the disclosed embodiments.

The present approach employs two dual-purpose sensors each capable of measuring two parameters of a monitored gas. One example of such dual-purpose sensors is ultrasonic sensors, which may be capable of concurrently measuring flow and concentration of a gas or other fluid. In one implementation of the present approach, ultrasonic sensors are employed and each ultrasonic sensor is associated with a gas conduit with an input and output, upon which at least a pair of ultrasonic transducers of the sensor are positioned such that sound traveling between the transducers is influenced by the flow and composition of gas within the conduit.

The transducers may be operated by one of (or a combination of) software executed on a suitable microprocessor and/or an application specific integrated circuit (ASIC). Such electrical components may be located within or proximate the sensor or remote from, but in communication with, the sensor, such as in a controller or control interface. By way of example such electronics and/or software may, when in operation, generate electrical signals to excite the transducers and/or receive or readout corresponding or responsive electrical signals generated by the transducers. The signals acquired from the transducers may be processed into a measurement set for use by a gas mixer controller in accordance with the approach discussed herein. By way of example, the measurement set so generated may be used to determine one or both of a gas flow or gas concentration within the monitored volume.

Figure 1:
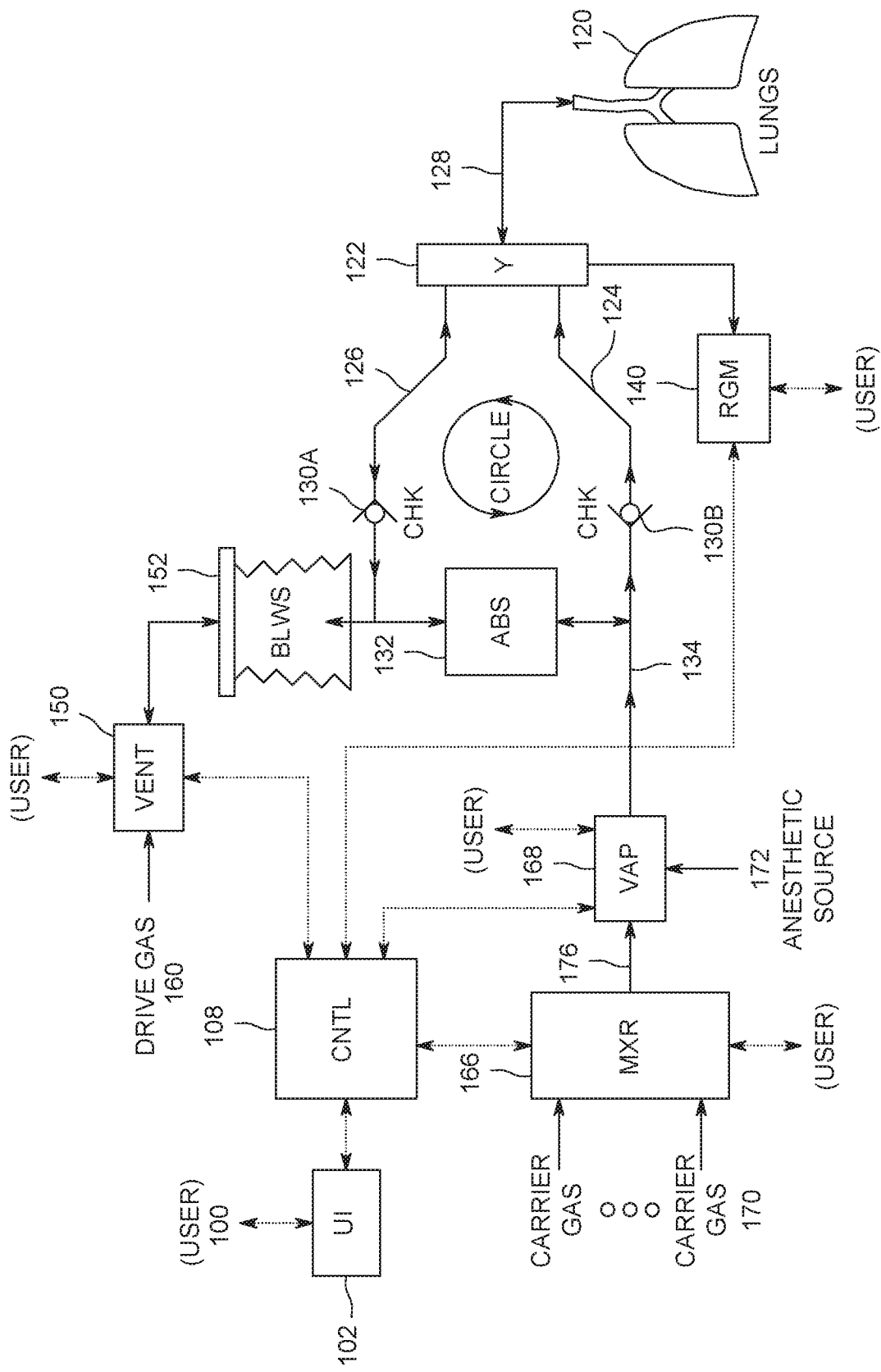
FIG. 1 depicts a general topology of an inhaled anesthesia administration, in accordance with aspects of the present disclosure.

With the preceding in mind, and to provide useful context and background, a general topology of an inhaled anesthesia administration is illustrated in FIG. 1. With reference to this figure, a clinician or user 100 interacts with a user interface 102 or various subsystems to direct an anesthesia machine to ventilate a patient's lungs 120 with an appropriate breathing gas mix. The user interface 102 or various subsystems provide for the acceptance of input from, and the provision of output to, the user 100. The user interface 102 communicates with a system controller 108, which directs or coordinates the various subsystems. At a low level, the depicted subsystems act on the gases in response to the commands received from the user 100 or via the controller 108 and/or measure parameters and pass them to the user 100 or to the controller 108 for processing and/or display.

As shown in FIG. 1, the patient and the target lungs 120 are connected to the machine with a patient breathing circuit configured in a Y arrangement 122. Gas flow coming from, and returning to, the machine travels in separate respective legs of the Y, while flow from/to the patient travels in the common leg 128 of the Y. On the machine side, gas to the patient flows in an inspiratory limb 124, and gas returning from the patient travels in an expiratory limb 126. Gas is directed to the appropriate limb through the action of flow check valves 130 placed in each. Often, the limbs are connected through an absorber 132, which routes the gas from the expiratory limb 126 back to the inspiratory limb 124, while passing the gas through a material to remove the exhaled carbon dioxide from the patient. This arrangement is known as a circle system, with recirculating gas flow as indicated. In some implementations, a respiratory gas monitor (RGM) 140 may be present to sample gas inspired and expired by the patient. Such an RGM 140 may be positioned in the patient breathing circuit for the purpose of measuring gas parameters and reporting them to the user interface 102 or possibly directly by the monitor.

Often during the practice of anesthesia, mechanical assistance is used to drive breathing gases into and receive gas out of the patient's lungs 120, thus facilitating recirculation. For example, in the depicted implementation, the ventilator 150 coordinates operation of a gas bellows 152 to deliver gas during inspiration and to receive gas during expiration. During inspiration, the ventilator 150 contracts the bellows 152, closing the check valve 130A in the expiratory limb 126 and opening the check valve 130B in the inspiratory limb 124. Gas in the bellows 152 then flows through the absorber 132 and down the inspiratory limb 124 to the patient. During expiration, the ventilator 150 allows the bellows 152 to expand, closing the check valve 130B in the inspiratory limb 124 and opening the check valve 130A in the expiratory limb 126. The bellows 152 then fills with gas from the patient in addition to upstream replenishment gas from the fresh gas limb 134. The ventilator 150 drives the bellows 152 in response to communication with the user 100 or controller 108, often using a pressured drive gas source 160.

As gas is consumed by the patient via uptake in the lungs 120, it is replaced. This is accomplished by the action of the medical gas mixer 166 and medical vaporizer 168. The gas mixer 166 may be connected to a number of gas sources 170 at its inputs, and acts to select and mix these gases to create both a gas flow and component gas concentration consistent with communications with the user 100 or controller 108. The output of the gas mixer 166 is connected to the input of the vaporizer 168 such that the gas from the mixer 166 becomes the carrier gas for the anesthetic gas produced by the vaporizer 168. An anesthetic source 172 is input to the vaporizer 168, which serves to convert the anesthetic to gas form if needed and mix it with the carrier gas to a concentration consistent with communications with the user 100 or the controller 108. The output of the vaporizer 168 is connected to the fresh gas limb 134.

Figure 2:
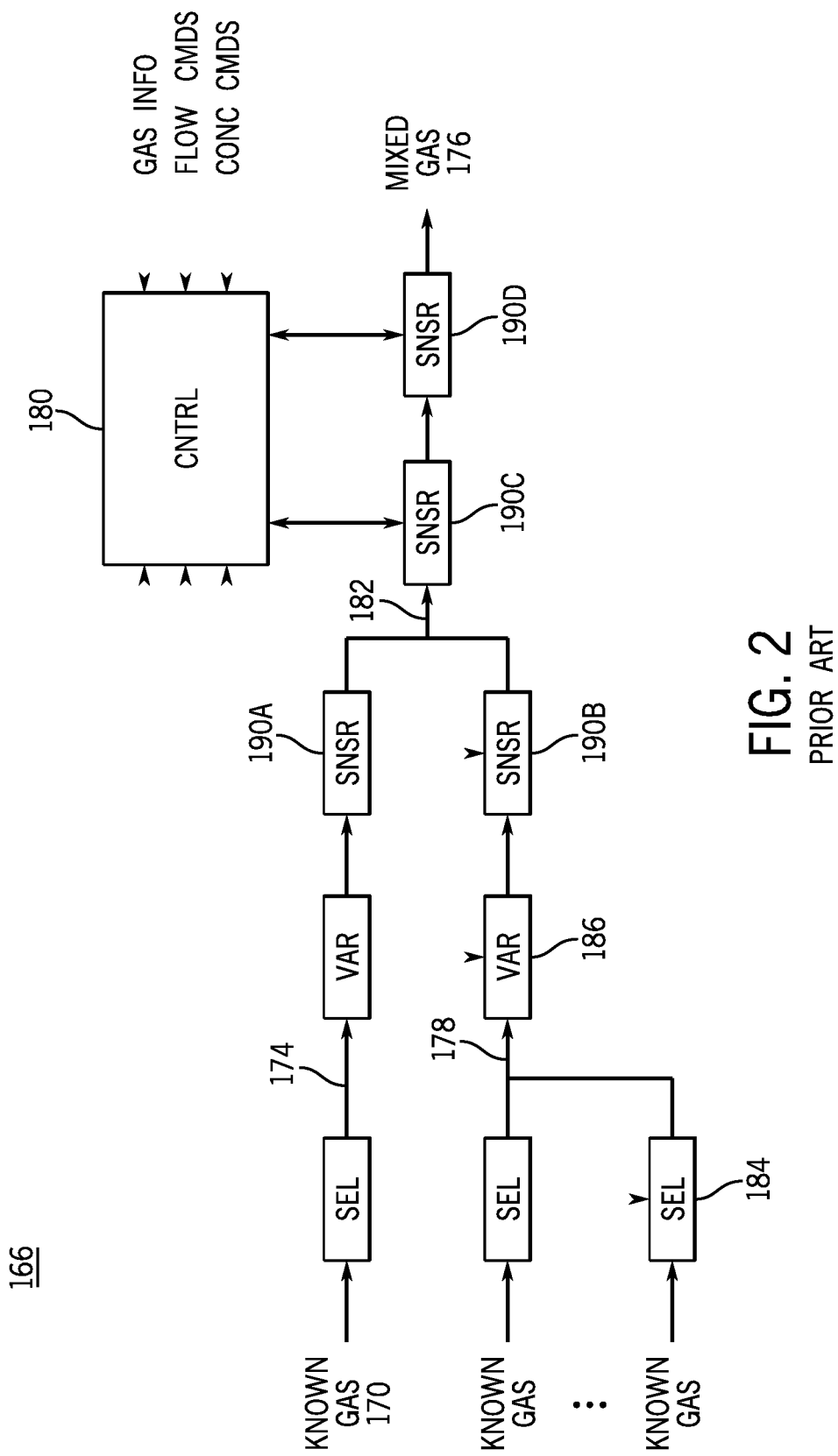
FIG. 2 depicts a topology of a conventional gas mixer.

With the preceding general overview in mind, aspects of the present approach related to the operation of the gas mixer 166 are described. A topology of a conventional medical gas mixer is shown in FIG. 2. In such a conventional approach, a gas mixer typically blends together two or more known gases 170 in a pairwise manner. Each gas is generally separately sourced and input via a respective gas mixer input. After blending, the gases are output as a mixed gas 176 at a mixed gas channel 182 output and administered to a patient as described above.

Typically, one gas is designated for a main gas channel 174 and one for a side gas channel 178. A mixer controller 180 (which may be a separate controller or a function performed by system controller 108) either knows the identity and/or properties of the gases that the mixer inputs are pre-configured with, or receives such information during real time operation. The mixer controller 180 uses this information, along with flow and/or concentration commands, which may come from the user 100 or system controller 108, to determine the current mixer operating state and compute the internal action required to achieve its desired operating state. Commands to the gas mixer 166 may be from a number of possible combinations of component and/or mixed gas flows, and/or mixed gas concentrations.

To perform the commanded mixing operation, the mixer controller 180 operates the selector valves 184 to pick the desired input gases to mix. In addition, the mixer controller 180 operates the variable valves 186 to achieve the commanded flows and/or concentrations in response to feedback measurements from separate flow and/or concentration sensors 190. While selector valves 184 are typically not calibrated for a particular gas, the variable valves 186 and/or sensors 190 typically are. If information about the input gas identity and/or properties is lost or does not match the available calibration of variable valve 186 and/or sensor 190, the accuracy and possibly safety of the gas mixer 166 may be compromised. Popular flow sensors such as are presently available can be calibrated for multiple gases at additional cost.

In a conventional topology, the sensors 190A, 190B in the main and side channels 174, 178 are typically gas flow sensors. The sensors 190C, 190D in the mixed channel 182 are typically either gas flow or gas concentration sensors. In order to control the flow and/or concentration in the main, side, and/or mixed channels, a total of at least two separate sensors 190 from the four locations shown in FIG. 2 are needed. As a matter of patient safety, a gas mixer 166 is often designed to have an additional, independent redundant measurement of flow and/or concentration, making the total number of separate sensors 190 needed to be at least three separate sensors 190 from the four locations shown. Further, mixer implementations that employ separate sensors 190 on the side, main, and/or mixed channels, as shown in FIG. 2, typically require information of each sensor's local environmental conditions with precision, due to the impact of differential temperatures on overall gas mixer accuracy. These various factors may contribute to additional cost of the gas mixer.

For the purpose of controlling a gas mixing operation, the mixer controller 180 computes targets for the measurements for its internal sensors based on the commands it receives from the user 100 or system controller 108. These targets may be in high-level terms, such as gas flow or gas concentration, or they may be in other intermediate or low-level terms, depending on the scheme chosen. The target flows and/or concentrations may be achieved using a feedback control scheme, where the controller 180 operates the variable valves 186 to minimize the difference or error between the target and measured sensor values. An example for flow is shown below in Equation (1), where the feedback error for the flow in the mixed channel ($e_{FX}$) is formed from the target for the flow in the mixed channel ($F_{TX}$) and the measured flow in the mixed channel ($F_{MX}$).

$$e_{FX} = F_{TX} - F_{MX} \quad (1)$$

An example for concentration is shown below in Equation (2), where the feedback error for the concentration in the mixed channel ($e_{cX}$) is formed from the target for the concentration in the mixed channel ($c_{TX}$) and the measured flows in the main channel ($F_{MM}$) and the mixed channel.

$$e_{cX} = c_{TX} - \frac{F_{MM}}{F_{MX}} \quad (2)$$

Note that other effective feedback error terms and controls schemes are possible (depending on the choices made for placement of sensors, combination of targets and measurements, and error comparison), and the present examples are provided solely to provide context and to facilitate explanation.

The mixer controller 180 typically has a check to detect and/or react to an improper concentration in the mixed gas channel 182 in the event of a single-fault failure. This may involve comparing the redundant flow and/or concentration to either: (1) the measured flow and/or concentration or (2) the target flow and/or concentration. An example is shown below in Equation (3), where the safety check for concentration in the mixed channel ($s_{cX}$) is formed from the target for concentration in the mixed channel, the measured flow in the mixed channel, and the redundant flow in the side channel ($F_{RS}$).

$$s_{cX} = c_{TX} - \left(1 - \frac{F_{RS}}{F_{MX}}\right) \quad (3)$$

As with the discussion relating to feedback error terms and control schemes, other effective checks are also possible, depending on the choices made for placement of sensors, combination of targets, measurements, and/or redundant measurements, and check comparison. When the check exceeds safety limits, the mixer controller 180 may perform a number of actions including, but not limited to, generating an alarm, shutting down, enabling alternate gas delivery, and so forth.

As noted above, as a practical matter, typically sensors 190 are single-purpose and need to be present in at least three of the four locations shown in FIG. 2 to provide the needed gas flow and gas concentration for control of the gas mixer 166 and for a useful degree of redundancy.

As discussed below, the present approach utilizes a different gas mixer topology. The described topology incorporates dual-purpose sensors, as discussed herein, each capable of simultaneously providing multiple data or measurements, such as for both gas flow and gas concentration. Any type of sensor capable of simultaneously providing both gas flow and gas concentration may be employed in accordance with the present approach. One example of such a dual-purpose sensor is an ultrasonic sensor, as discussed herein, and the present examples and discussion are presented in the context of such an ultrasonic sensor. It should be appreciated, however, that such examples are provided only for the purpose of explanation and to provide a useful, real world context and that other suitable sensors are also encompassed by the present discussion.

With respect to ultrasonic sensors, such sensors operate based on principles related to sound propagation. With respect to these underlying concepts, sound (which may be understood to be the propagation of acoustic waves in a medium) is influenced by both gas flow and gas composition, the latter being directly related to individual gas component concentration. In particular, the longitudinal speed of propagation of the acoustic waves, i.e., the speed-of-sound, is influenced by both flow and concentration of the medium through which the waves propagate.

A simple physics model (Equation (4)) of the speed-of-sound (v) in a gas flowing at flow rate (F) is shown below, having two terms, one ($v_{in}$) related to the flow rate, and the other ($v_s$) related to the gas medium's properties. The effect of gas flow may increase or decrease the overall speed-of-sound and is modulated by inclination angle (α) depending on the direction of sound relative to the direction of gas flow.

$$v = v_s \pm v_m \sin\alpha \quad (4)$$

The first term ($v_s$) depends on heat capacity ratio (γ) and molar mass (M), having values which are characteristic of each gas, as well as gas temperature (T) as shown in Equation (5) below. Also included is the molar gas constant (R).

$$v_s = \sqrt{\frac{\gamma RT}{M}} \quad (5)$$

Properties of mixed gases can be related back to those of the component gases ($\gamma_1$, $M_1$, $\gamma_2$, $M_2$) as shown in Equations (6, 7) below and through the gas concentration (c) of either component.

$$\gamma = 1 + \left(\frac{c}{\gamma_1 - 1} + \frac{1-c}{\gamma_2 - 1}\right)^{-1} \quad (6)$$

$$M = cM_1 + (1-c)M_2 \quad (7)$$

The second term ($v_m$) depends on the flow rate and the cross-sectional area (A) of the gas conduit as shown below.

$$v_m = \frac{F}{A} \quad (8)$$

Time-of-flight (t) may be measured using ultrasonic transducers and appropriate electronics and software. Speed-of-sound can be related to the sound path length (d) as shown below.

$$v = \frac{d}{t} \quad (9)$$

Figure 3:
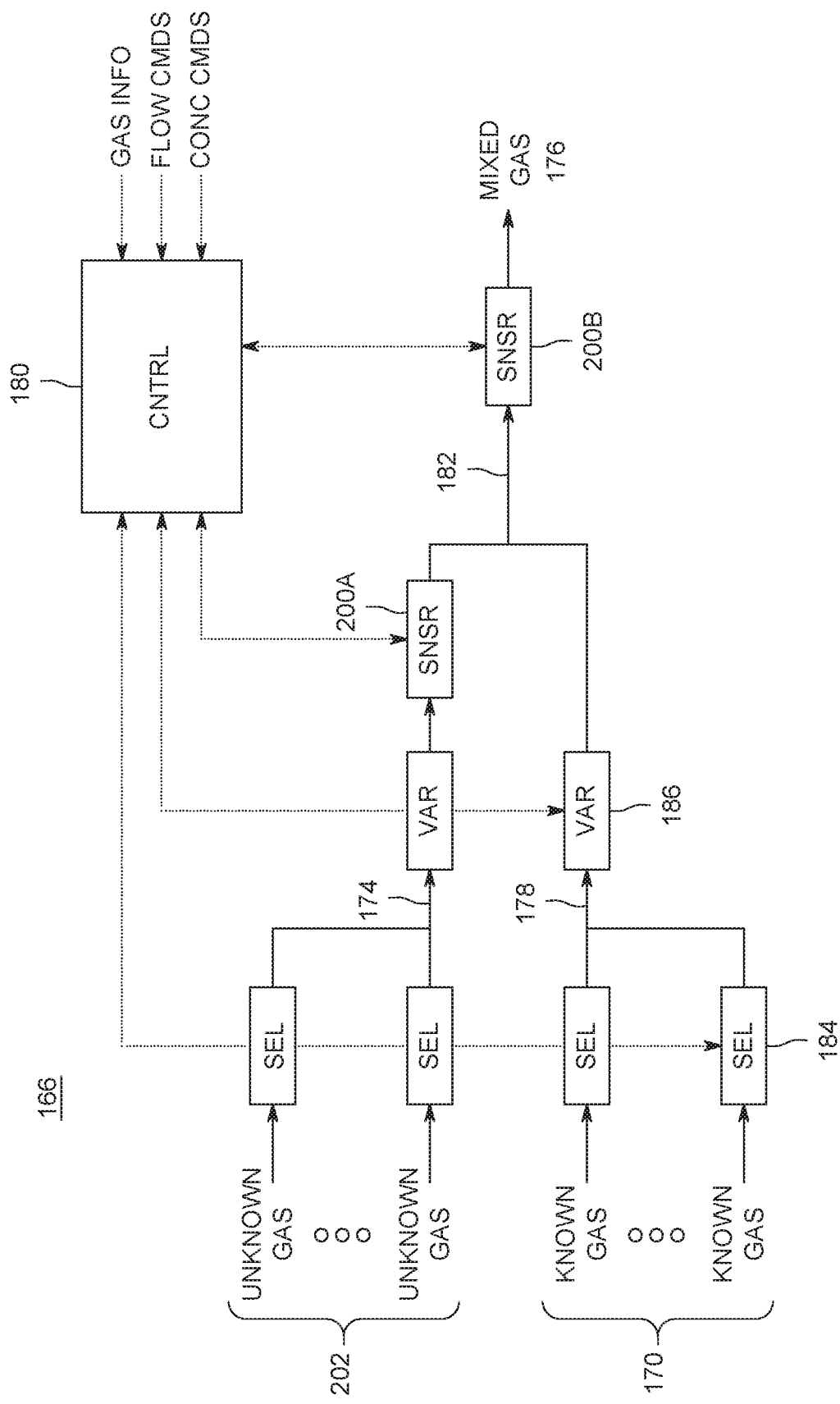
FIG. 3 depicts a topology of gas mixer, in accordance with aspects of the present disclosure.

With the preceding in mind, and turning to FIG. 3, a topology for a medical gas mixer 166 is depicted in accordance with the present approach. In the depicted topology, a pair of dual-purpose sensors, such as two ultrasonic sensors 200 are employed. In this topology, a set of two or more gases are sourced at their respective mixer inputs and blended together pairwise, with the resulting mixed gas 176 provided at a mixed gas channel 182 output. Examples of gases that may be provided as input streams to the gas mixer 166 include, but are not limited to, oxygen, air, nitrous oxide, carbon dioxide, heliox, xenon, and so forth). As used herein, the term "gas" should be understood to encompass not only a pure gas stream, but also gas blends that may be either inputs or outputs to the gas mixer 166. In one implementation, there is a main gas channel 174 through which one gas 202 is input and a side gas channel 178 through which as second gas 170 is input. The mixer controller 180 either knows the identity and/or properties of the gases 170 in the side gas channel 178 that the mixer inputs are pre-configured with, or receives such information during real time operation. The gases 202 in the main gas channel 174 can be (but are not necessarily) unknown and may even be of variable composition. The mixer controller 180 uses the known information, along with flow and/or concentration commands from the user 100 or system controller 108, to determine the current mixer operating state and compute the internal action required to achieve its desired operating state. Commands to the mixer controller 180 may be from a number of possible combinations of component and/or mixed gas flows, and/or mixed gas concentrations.

The mixer controller 180 is configured and/or programmed to operate the selector valves to pick the desired input gases to mix. The mixer controller 180 is also configured and/or programmed to operate the variable valves to achieve target gas flows and/or gas concentrations in response to feedback measurements from the dual-purpose sensors (e.g., ultrasonic sensors 200) located in the main (i.e., ultrasonic sensor 200A) and mixed (i.e., ultrasonic sensor 200B) gas channels. As the mixer controller 180 does not need to know the identity and/or properties of the gas 202 in the main gas channel 174, the gas 202 can be any number of possible gases, or even of variable composition. That is, in this topology, the accuracy and safety of the medical gas mixer 166 are virtually independent of the main channel 174 gas.

As shown in the depicted example, in order to control the gas flow and/or gas concentration in the main, side, and/or mixed gas channels, only the two separate sensors 200A and 200B in the locations shown (i.e., one positioned in the main gas channel 174 and one positioned in the mixed gas channel 182) are required. The independent redundant measurement of gas concentration remains available due to the dual nature of the sensors 200. Thus, in this topology no additional sensors are required for patient safety, which may reduce hardware cost.

In one implementation, the gases in the sensors 200 in the main and mixed gas channels 174, 182 may be pre-conditioned to have the same temperature, which can then be measured as a lower-precision, common-mode temperature, while still preserving medical gas mixer accuracy. Such pre-conditioning may be accomplished a number of ways. By way of example, in one embodiment, the gas flow is routed through a passage of suitable length in a manifold having a known or specified heat conductivity. Due to the relatively low heat capacity of a gas, and through interaction with the walls of the passage in the manifold, the gas equalizes to the temperature of the manifold. The manifold may be heated, cooled, and/or simply maintained at local ambient temperature. In one embodiment, the main and mixed channel 174, 182 gas flows are routed in separate passages in a common metal manifold that is maintained at local ambient temperature.

In addition, separate temperature and/or pressure transducers may be provided in one or more of the gas channels to obtain one or both of temperature or pressure of the gas in the respective channel. Further, if temperature transducers are provided in combination with the manifold pre-conditioning arrangement as described above, the temperature transducers may be located so as to transduce the temperature of the manifolds in the main and/or mixed channels 174, 182 and/or to transduce the temperature of the common metal manifold. If temperature and/or pressure measurements are obtained from such transducers, they may also be provided to the mixer controller 180 for use in control and feedback calculations performed by the mixer controller 180.

Figure 4:
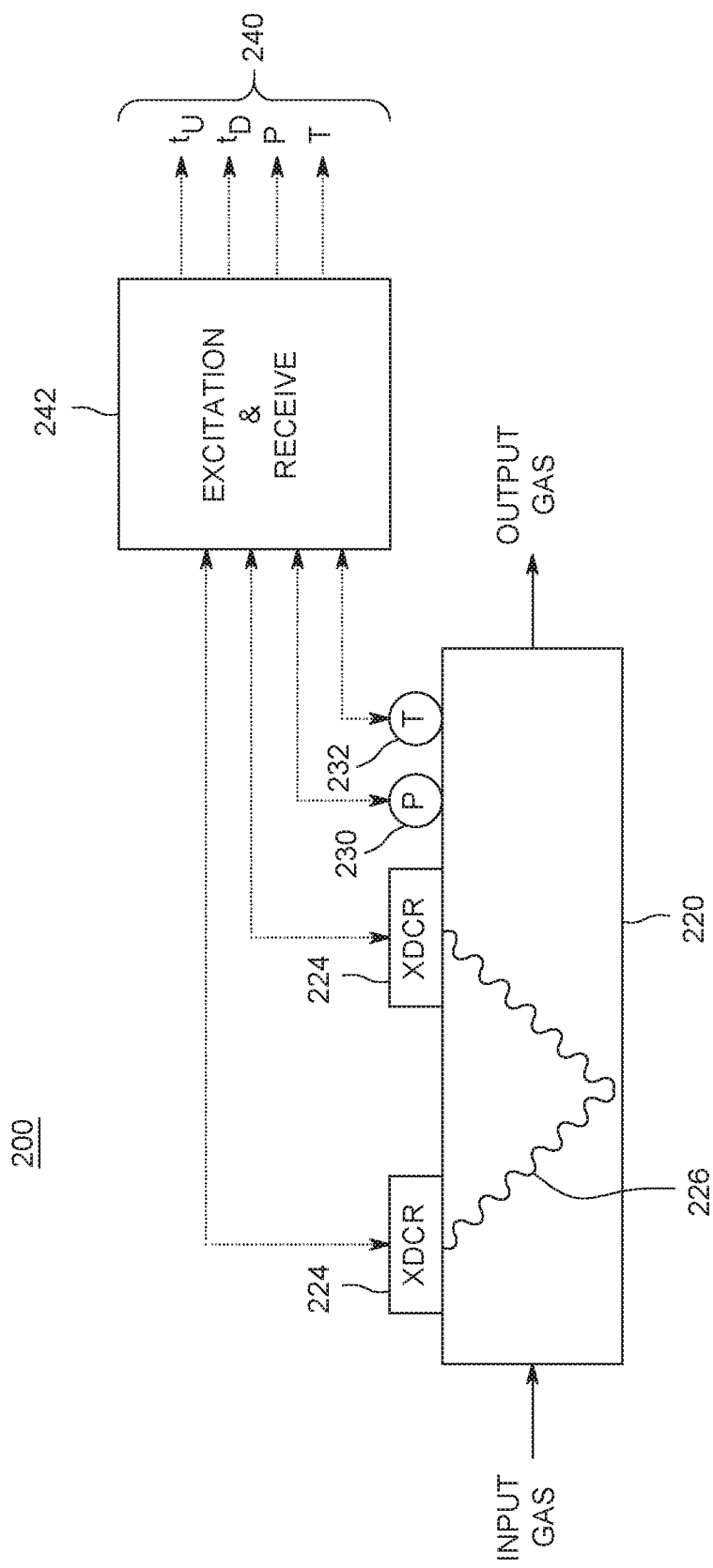
FIG. 4 depicts a schematic of a dual-purpose sensor, in accordance with aspects of the present disclosure.
Figure 5:
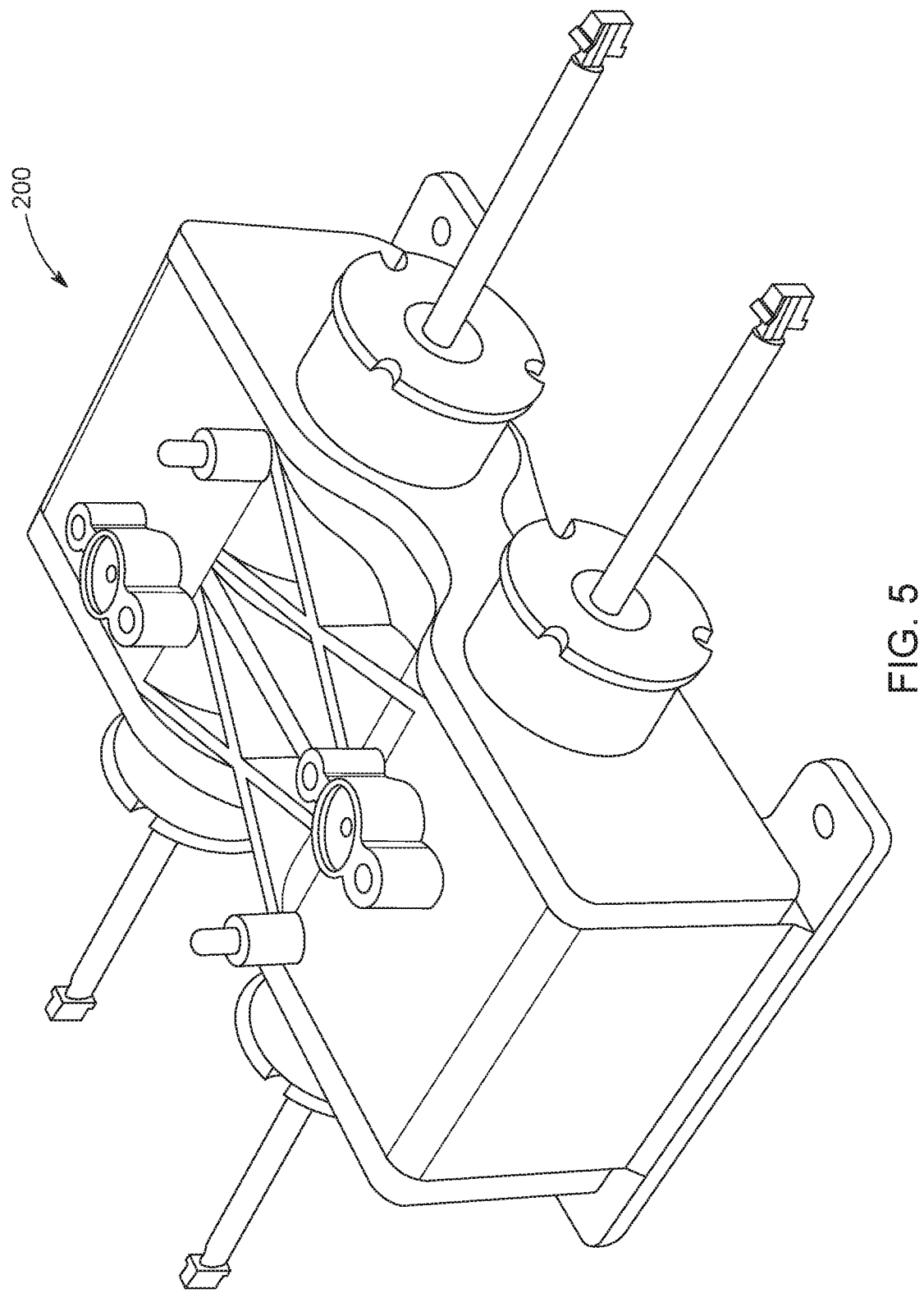
FIG. 5 depicts a perspective view of a physical implementation of a dual-purpose sensor, in accordance with aspects of the present disclosure.

Turning to FIG. 4, an example of a dual-purpose sensor in the form of an ultrasonic sensor 200 is depicted. For reference, a perspective external depiction of a physical embodiment of two adjacently-packaged sensors 200 is provided in FIG. 5. In the depicted example, each ultrasonic sensor 200 includes a gas conduit 220 with an input and output, upon which at least a pair of ultrasonic transducers 224 are positioned such that sound 226 traveling between the transducers 224 is influenced by the gas flow and gas composition in the conduit 220. A temperature transducer 232 and/or pressure transducer 230 may, in certain embodiments, be included to sense the local environmental conditions of the gas in the conduit 220. Depending on the implementation, the transducers 224, 230, 232 may be placed in any number of locations and/or orientations to be effective.

The transducers 224, 230, 232 may be operated by one of (or a combination of) software executed on a suitable microprocessor and/or an application specific integrated circuit (ASIC). Such electrical components may be located within or proximate the sensor 200 or remote from, but in communication with, the sensor 200, such as in a controller (e.g., mixer controller 180) or control interface. By way of example such electronics and/or software (illustrated generally as excitation and receive circuitry 242) may, when in operation, generate electrical signals to excite (or otherwise activate or operate) the transducers and/or receive or readout corresponding or responsive electrical signals generated by the transducers. The signals acquired from the transducers may be processed into a measurement set 240 for use by the mixer controller 180. In one embodiment, the measurement set 240 includes an upstream time-of-flight ($t_U$) and a downstream time-of-flight ($t_D$), in addition to possibly any one or more of a temperature (T) or a pressure (P).

The aforementioned time-of-flight measurements may be used to calculate measurements of the flow and/or concentration of the gas in the sensor 200. In some embodiments, one or more of temperature and pressure measurements may also be employed in the gas flow and/or concentration calculations though, as noted above, temperature and pressure measurements are not required.

In the following discussion, "$f( )$" denotes "is a function of". Measurements having an associated "M" subscript relate to the main gas channel 174, while those with an associated "X" subscript relate to the mixed gas channel 182. As discussed below, gas flow may be calculated using upstream and downstream time-of-flight alone or, in certain embodiments, may incorporate some or all of the other measurements that may be present in a given sensor's measurement set 240. Thus, main gas flow (Equation (10)) and mixed gas flow (Equation (11)) may be given as:

$$F_M = f(t_{UM}, t_{DM}, T_M, P_M) \tag{10}$$

$$F_X = f(t_{UX}, t_{DX}, T_X, P_X) \tag{11}$$

The time-of-flight measurements, either alone or in combination with temperature and/or pressure measurements, may also be used to calculate a measurement of the concentration (Equations (11, 12)) of the component gases in the respective conduits. In particular, the concentration of component gases in one or both of the main gas channel 174 or mixed gas channel 182 as a function of the time-of-flight measurements noted herein may be calculated. For the main gas channel 174, this is accomplished using at least one of the upstream or downstream time-of-flight measurements from sensor 200A. For the mixed gas channel 182, this is accomplished using at least one of the upstream or downstream time-of-flight measurements from each sensor 200. Other possible combinations of time-of-flight measurements are also effective for this calculation. In addition, temperature measurements (if available) may also be employed in the gas concentration calculation, as shown below. As noted above, however, temperature measurements are not necessary for the calculation.

$$c_M = f(t_{UM}, T_M) \tag{11}$$

$$c_X = f(t_{UM}, t_{UX}, T_M, T_X) \tag{12}$$

With this in mind, for the purposes of control, the mixer controller 180 computes targets for the flow and/or concentration measurements from its internal sensors 200 based on the flow and/or gas concentration commands it receives from the user 100 or system controller 108. The target flows and/or concentrations are achieved using a feedback control scheme, where the controller 180 operates the variable valves 186 to minimize the difference or error between the target and measured sensor values. As discussed herein, the feedback error for the flow in the mixed channel ($e_{FX}$) is formed from the target for the flow in the mixed channel ($F_{TX}$) and the measured flow in the mixed channel ($F_{MX}$), as discussed above with respect to Equation (1).

An example for concentration is shown below, where the feedback error for concentration in the mixed channel ($e_{cX}$) is formed from the target for the concentration in the mixed channel ($c_{TX}$) and the measured concentration in the mixed channel ($c_{MX}$).

$$e_{cX} = c_{TX} - c_{MX} \tag{13}$$

Other effective feedback error terms and controls schemes are also possible, depending on the choices made for combination of targets and measurements, and error comparison.

For the purpose of safety, the mixer controller 180 may be provided with a check to detect and/or react to an improper concentration in the mixed gas channel 182 in the event of a single-fault failure. Such a check may involve comparing the measured concentration to the measured flow in the main gas channel 174 and/or the measured flow in the mixed gas channel 182, as shown in the example below (Equation (14)). While the same sensor 200B in the mixed gas channel 182 may be used for both control and safety purposes, the dual nature of the sensor 200B to provide both flow and concentration measurements is still effective in single-fault conditions because of the disparity in effect on speed-of-sound, and therefore time-of-flight, that flow and concentration have.

$$s_{cX} = f(c_{MX}, F_{MM}, F_{MX}) \tag{14}$$

When the check exceeds safety limits, the mixer controller 180 may perform a number of actions including, but not limited to, generating an alarm, shutting down, enabling alternate gas delivery, and so forth.

Technical effects of the invention include providing a medical gas mixer design that is accurate and safe independent of the gas in its main gas channel. In one embodiment, dual-purpose sensors, such as ultrasonic sensors, are employed, such as in a configuration in which one is positioned in the mixed gas flow channel and one is positioned in the main gas flow channel. Each sensor provides measurements that may be used to determine both gas flow and gas concentration in the respective channel, even when the identity and/or properties of the gas in the main gas channel are unknown.

This written description uses examples to disclose the invention, including the best mode, and also to enable any person skilled in the art to practice the invention, including making and using any devices or systems and performing any incorporated methods. The patentable scope of the invention is defined by the claims, and may include other examples that occur to those skilled in the art. Such other examples are intended to be within the scope of the claims if they have structural elements that do not differ from the literal language of the claims, or if they include equivalent structural elements with insubstantial differences from the literal languages of the claims.

The invention claimed is:

1. A method for regulating operation of a medical gas mixer, comprising:
   flowing a first gas through a main gas channel;
   flowing a second gas through a side gas channel;
   combining the first gas and the second gas to form a mixed gas in a mixed gas channel;
   concurrently generating a first set of measurements for a plurality of different parameters using a first dual-purpose sensor in the main gas channel and concurrently generating a second set of measurements for the plurality of different parameters using a second dual-purpose sensor in the mixed gas channel;
   calculating one or more of flow of the first gas, flow of one or more components of the first gas, or concentration of one or more components of the first gas using only one or both of the first set of measurements and the second set of measurements;
   calculating one or more of flow of the mixed gas, flow of one or more components of the mixed gas, or concentration of one or more of the components of the mixed gas using only the second set of measurements or both the first set of measurements and the second set of measurements; and
   controlling operation of valves in both the main gas channel and the side gas channel based only upon one or more of the calculated flows or concentrations.

2. The method of claim 1, further comprising:
   comparing one or more of flow of the first gas, flow of one or more components of the first gas, flow of the mixed gas, or flow of one or more components of the mixed gas to target flow values and to control operation of valves based upon this comparison.

3. The method of claim 1, further comprising:
   comparing the concentration of one or more components of the mixed gas to target concentration values and to control operation of valves based upon this comparison.

4. The method of claim 1, wherein at least one of the first set of measurements or the second set of measurements comprises one or more time-of-flight measurements.

5. The method of claim 1, wherein the first dual-purpose sensor and the second dual-purpose sensor comprise ultrasonic sensors.

6. The method of claim 1, wherein the plurality of different parameters comprises gas flow and gas concentration.

7. A medical gas mixer, comprising:
   a main gas channel comprising one or more main control valves that during operation control a first flow of a first gas through the main gas channel;
   a side gas channel, comprising one or more side channel control valves that during operation control a second flow of a second gas through the side gas channel;
   a mixed gas channel configured to receive the first flow of the first gas and the second flow of the second gas during operation and to output a mixed gas;
   a first dual-purpose sensor positioned in the main gas channel and configured to concurrently generate a first set of measurements for a plurality of different parameters during operation;
   a second dual-purpose sensor positioned in the mixed gas channel and configured to concurrently generate a second set of measurements for the plurality of different parameters during operation; and
   a gas mixer controller configured to receive the first set of measurements and the second set of measurements, to calculate, one or more of flow of the first gas, flow of one or more components of the first gas, or concentration of one or more components of the first gas based only on one or both of the first and second sets of measurements, to calculate, one or more of flow of the mixed gas, flow of one or more components of the mixed gas, or concentration of one or more components of the mixed gas based only on the second set of measurements or both of the first and second sets of measurements, and to control operation of the main gas channel control valves and the side gas channel control valves based solely upon one or more of the calculated flows or concentrations.

8. The medical gas mixer of claim 7, wherein the gas mixer controller is configured to compare one or more of, flow of the first gas, flow of one or more components of the first gas, flow of the mixed gas, or flow of one or more components of the mixed gas, to corresponding target flow values and to control operation of one or more of the main gas control valves or the side gas channel control valves based upon this comparison.

9. The medical gas mixer of claim 7, wherein the gas mixer controller is configured to compare one or more of concentration of one or more components of the first gas or concentration of one or more components of the mixed gas to target concentration values and to control operation of one or more of the main gas control valves or the side gas channel control valves based upon this comparison.

10. The medical gas mixer of claim 7, wherein no sensor is positioned in the side gas channel.

11. The medical gas mixer of claim 7, wherein at least one of the first set of measurements or the second set of measurements comprises one or more time-of-flight measurements.

12. The medical gas mixer of claim 7, wherein the first dual-purpose sensor and the second dual-purpose sensor comprise ultrasonic sensors.

13. The medical gas mixer of claim 12, wherein the ultrasonic sensors each comprise a pair of ultrasonic transducers.

14. The medical gas mixer of claim 12, wherein the ultrasonic sensors further comprise one or both of a pressure transducer or a temperature transducer.

15. The medical gas mixer of claim 7, wherein one or both of the identity or properties of the second gas are known to the gas mixer controller.

16. The medical gas mixer of claim 7, wherein the first gas comprises a pure gas, and only the first gas flows in the main gas channel.

17. The medical gas mixer of claim 7, wherein the plurality of different parameters comprises gas flow and gas concentration.

* * * * *